(12) United States Patent
Telischi et al.

(10) Patent No.: US 6,640,121 B1
(45) Date of Patent: Oct. 28, 2003

(54) OTIC MICROPROBE FOR NEURO-COCHLEAR MONITORING

(75) Inventors: Fred Telischi, Coral Gables, FL (US); Ozcan Ozdamar, Miami, FL (US); Jean-Marie Parel, Miami Shores, FL (US); Fabrice Manns, Coral Gables, FL (US)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 09/635,395

(22) Filed: Aug. 10, 2000

Related U.S. Application Data

(60) Provisional application No. 60/147,822, filed on Aug. 10, 1999.

(51) Int. Cl.$^7$ .............................. A61B 5/04; A61B 5/026
(52) U.S. Cl. ................... 600/379; 600/478; 600/504; 600/559
(58) Field of Search ............................. 600/379, 559, 600/478, 504

(56) References Cited

U.S. PATENT DOCUMENTS

| | | | | |
|---|---|---|---|---|
| 4,706,682 A | * | 11/1987 | Stypulkowski et al. | 600/379 |
| 4,781,196 A | * | 11/1988 | Killion | 600/379 |
| 5,419,312 A | * | 5/1995 | Arenberg et al. | 600/108 |
| 6,007,494 A | * | 12/1999 | Zenner et al. | 600/559 |
| 6,264,603 B1 | * | 7/2001 | Kennedy | 600/25 |

OTHER PUBLICATIONS

Telischi et al., "Distortion–Product Otoacoustic Emission Monitoring of Cochlear Blood Flow", Laryngoscope 108 (Jun. 1998), pp. 837–842.

Stern et al., "Continuous Measurement of Tissue Blood Flow by Laser–Doppler Spectroscopy", Am. J. Physiol. 232(4) (1977); pp. H441–H448.

Levine et al., "Monitoring Auditory Evoked Potentials During Acoustic Neuroma Surgery", Ann Otol Rhinol Laryngol 93 (1984); pp. 116–123.

Ben et al., "Dynamic Response of Cochlear Blood Flow to Occlusion of Anterior Inferior Cerebellar Artery in Guinea Pigs", J. Appl. Physiol. (76)(1) (1994); pp. 212–217.

Mom et al., "Measuring the Cochlear Blood Flow and Distortion–Product Otoacoustic Emissions During Reversible Cochlear Ischemia: A Rabbit Model", Hearing Research 133 (1999), pp. 40–52.

Kilpatrick et al., "Blood Velocity Measurement by Fiber Optic Laser Doppler Anemometry", IEEE Transactions on Biomedical Engineering, vol. BME–29, No. 2, (1982), pp. 142–145.

Levine, "Surgical Monitoring Applications of the Branstem Auditory Evoked Response and Electrocochleography", Clinical Atlas of Auditory Evoked Potentials (1998), pp. 103–116.

* cited by examiner

*Primary Examiner*—Lee Cohen
(74) *Attorney, Agent, or Firm*—Nixon & Vanderhye P.C.

(57) ABSTRACT

A microprobe useful for assessing auditory function by enabling clinical and intraoperative measurements of blood flow, particularly cochlear blood flow and neural compound action potentials, particularly of the auditory nerve (cranial nerve VIII) is disclosed. In addition, a monitoring system containing this microprobe and a method of using the microprobe are described.

40 Claims, 5 Drawing Sheets

OTIC MICROPROBE FOR NEURO-COCHLEAR MONITORING

CROSS-REFERENCE TO RELATED APPLICATION

This application is based on Provisional Application No. 60/147,822, filed Aug. 10, 1999, which disclosure is incorporated herein by reference.

BACKGROUND OF THE INVENTION

1. Field of the Invention

The invention relates to a microprobe useful for assessing auditory function by enabling clinical and intraoperative measurements of blood flow, particularly cochlear blood flow and neural compound action potentials, particularly of the cochlea and auditory (vestibulocochlear) nerve, also known as cranial nerve VIII.

2. Description of Related Art

Interruption of cochlear blood flow and damage to the auditory nerve have been implicated as the primary causes of sensory hearing loss that may occur during acoustic neuroma tumor removal. Neurosensory monitoring involving electrophysiological signals and continuous blood flow measurements have been proposed to save the hearing of patients undergoing such procedures. The most commonly monitored electrophysiological signals are the auditory brainstem response (ABR) and the compound action potential (CAP) of cranial nerve VIII. Each of these traditionally targeted signal sources have drawbacks, making theses sources less than optimal for mitigating hearing loss.

Auditory brainstem response is the most easily applied procedure and is noninvasive, yet suffers from low signal to noise ratios (SNR). As a result, extensive averaging must be performed to generate usable data.

Measurement of compound action potentials provides better signal to noise ratios than may be obtained with auditory brainstem response. However, compound action potential monitoring requires invasive techniques for optimal recording conditions, and requires at least some averaging to obtain recognizable responses. Although both auditory brainstem response and compound action potentials provide critical information about the transfer of auditory information from the cochlea to the auditory nerve, they are not the best methods for monitoring cochlear ischemia due to delays in changes in the measures after alterations in cochlear blood flow. For example, due to metabolic reserve, changes in electrophysiological activity after an interruption of blood flow in the internal auditory artery take about 20–60 seconds.

Monitoring cochlear blood flow with laser-Doppler measurements has the potential to overcome some of the drawbacks of electrophysiological monitoring. Since it directly monitors blood flow to the cochlea, laser-Doppler does not succumb to metabolic reserve or prolonged signal averaging problems, and has been shown in animal models to follow changes in cochlear blood flow in near real time. The rapid feedback from laser-Doppler can provide surgeons with timely information regarding the effect of surgical maneuvers and vasospasm on cochlear blood flow, with the potential to reverse both cochlear ischemia and adverse hearing outcome.

Electrocochleography (EcochG) is a measure of the most peripheral of the neuroelectric auditory-evoked responses. The compound action potential component of the EcochG response represents the same activity as Wave I of the auditory brainstem response, and is the most useful for intraoperative monitoring. The EcochG has the advantage of being a near-field recording and as such requires fewer averages and less time to obtain a response. Detailed descriptions of stimulus and recording parameters are known in the art. The EcochG can be recorded from the external auditory canal or within the middle ear (transtympanic). Previous investigators have compared the time and number of sweeps required to obtain a response using both techniques. EcochGs recorded within the middle ear showed improved signal to noise ratios resulting in waveforms obtained with fewer sweeps over a shorter period of time. Positioning of the recording electrode at the round window provides the most robust response. The surface or subdermal reference electrode is placed in the midline between the vertex and forehead. Ground electrodes can be located near the recording electrodes at a convenient spot (e.g. ipsilateral shoulder or contralateral forehead).

The stimulus should be a broad band rarefaction click of high intensity (85 to 95 dBnHL) with a rate of 21.1 sec. An impedance of as high as 100 k$\Omega$ may be acceptable in a transtympanic (middle ear round window) montage as compared to the need for extremely low impedance of less than 5K$\Omega$ required for ear canal electrodes.

Adequate preoperative baseline responses must be obtained against which to judge changes observed during the procedure. Significant changes in compound action potentials indicate, and can be used to differentiate between, cochlear and neural injury. Twenty seconds or more must elapse before changes in the EcochG response can be detected. This delay presumably occurs as a result of metabolic reserves which sustain cochlear function until their depletion from prolonged ischemia causes failure of electrophysiologic activity.

When a parallel laser beam is incident on a medium containing randomly distributed particles, a fraction of the incident power is absorbed by the particles and a fraction is scattered, in theory at all angles. The angular intensity distribution of the scattered laser radiation depends mostly on the wavelength and geometry of the incident beam and on the distribution and size of the scattering particles. When the scattering particles are stationary, the scattering angle for each scattering event, and thus the spatial distribution of intensity, is stationary as well.

When the scattering particles move at any given velocity, the scattering angle varies with the particle velocity and with the angle between the direction of incidence and the direction of movement of the particle. As a result, the scattered light intensity measured in any direction is no longer stationary. The scattered signal contains a broad spectrum of frequencies which is a function, among others, of the particle velocity distribution and of the direction of the particles. A frequency analysis of the scattered intensity signal in a given direction provides information on the velocities of the particles. Because the frequency shifts when the speed or direction of the particles varies, this optical technique for flow measurement is called laser Doppler velocimetry.

Several optical configurations have been used for laser Doppler velocimetry. Laser Doppler velocimetry has been used in biology and medicine mostly as a noninvasive diagnostic tool to characterize blood flow in vitro and in vivo in the eye or percutaneous tissue.

The feasibility of using laser-Doppler velocimetry for in situ in vivo measurement of blood flow was demonstrated by several investigators by using an optical fiber design. In fiber optic laser Doppler velocimeters, the incident light signal is delivered to the measured tissue volume through a single multimode optical fiber (excitation fiber) with a diameter of 50 to 100 microns. The light scattered back by the tissue is collected either with the same optical fiber, or with one or two separate optical fibers (collecting fibers) located next to the excitation fiber. The light transmitted through the collecting fibers is sent to separate photodetectors connected to the signal processing unit. The main advantage of fiber optic laser Doppler velocimetry is that the excitation and collecting fibers can be integrated into a miniature hand held probe for minimally invasive in situ measurements of blood flow. The design of the probe can be adapted for different types of measurement conditions, including endoscopic measurements or measurements at 90 degrees.

The blood supply to the cochlea in humans and animals is provided by an end-artery branch of the internal auditory artery. Abolition of this blood supply results in a complete loss of auditory function in animals. Measurement of cochlear blood flow has been of experimental interest because cochlear ischemia is assumed to be one of the principal causes of certain types of presbycusis and for the many cases of sudden idiopathic sensorineural hearing loss (SNHL). Vascular compromise of the cochlea is commonly thought to cause some forms of sound-induced acoustic trauma. Additionally, some of the hearing loss encountered in patients with acoustic neuromas may also be caused by cochlear ischemia. In addition to the vascular-related effects of disease states on inner ear function, the tenuous nature of the cochlear blood supply becomes important during certain surgical procedures performed around the internal auditory canal/CPA (cerbellopontine angle) region and posterior fossa where post-operative hearing loss is thought to be due to compromise of the internal auditory artery.

Shortly after the initial reports of laser-Doppler measurements of blood flow in general, successful measures of cochlear blood flow using laser-Doppler were accomplished. Use of laser-Doppler systems makes it possible to routinely measure cochlear blood flow in experimental animal models, including the guinea pig. In such small laboratory species as gerbils and guinea pigs, the laser beam of these instruments can be easily directed toward the capillary bed if the stria vasculairs due to the translucency of the cochlea's bony capsule. In other animal species, such as rabbits and humans, in which the cochlea is embedded in dense temporal bone, the laser beam is greatly attenuated, thereby, adversely compromising its measurement capabilities.

In humans, to date, only a few experimental findings on laser-Doppler measures of cochlear blood flow are available. For example, some reports indicate that cochlear blood flow is measurable by positioning a laser-Doppler probe directly on the promontory cochlea. On this position, a transient decrease in cochlear blood flow was noted during breath holding. Those reports also indicate that the thick cochlear bone of the human attenuates the laser beam up to four times more than does the more translucent otic capsule of the guinea pig. Due to this reduced sensitivity, some investigators have concluded that the mucosal vasculature of the promontory contacting the probe likely contaminated some cochlear blood flow readings.

In a later study, other investigators also placed a laser-Doppler probe on the promontory of a few patients in order to measure cochlear blood flow under several conditions. Specifically, they showed that cochlear blood flow changed more dramatically during irrigation of the external ear canal with either warm or cold water than during electrical stimulation of the cochlea using an electrode on the round window membrane. However, the authors cautioned that movement related artifacts, which occurred mostly during the irrigation procedure, could have also contributed to the robust changes in cochlear blood flow they observed. Nonetheless, these authors were confident that their careful measurements avoided such contamination of the data.

In both studies noted above, cochlear function was not monitored simultaneously with cochlear blood flow measurements, and, for obvious ethical reasons, deliberate induction of transient ischemia in patients was not performed to test the validity of laser-Doppler cochlear blood flow changes. One opportunity to assess the sensitivity of laser-Doppler measures of cochlear blood flow in human cases of cochlear ischemia would be to monitor the blood flow to the cochlea during surgery to remove vestibular schwannomas, when, at time, an unplanned interruption of blood flow can occur. However, no such reports are currently known, mostly due to the fact that until recently, stable laser-Doppler cochlear blood flow baseline values have been difficult to obtain throughout the lengthy surgical procedures. The opacity of the cochlear bone over the promontory region likely precluded any sensitive laser-Doppler measurements.

Therefore, a need exists for improved means of measuring signals indicative of auditory function to reduce hearing loss during surgery and diagnose hearing loss in clinical settings.

SUMMARY OF THE INVENTION

A first embodiment of the invention is an integrated otic microprobe for atraumatically monitoring auditory function in a patient. The microprobe comprises a fiber optic laser Doppler flowmetry probe which measures blood flow and velocity, an electrocochleography electrode which measures neural compound action potentials, and a cap encompassing a tip of the fiber optic laser Doppler flowmetry probe. Also included in the microprobe is at least one irrigation lumen, at least one aspiration lumen, and a means for conducting an electrocochlear signal from the laser Doppler flowmetry probe tip encompassed by the cap to a computerized data monitoring unit. The integrated otic microprobe may further comprise a flexible endoscope, in which case the microprobe has a diameter of less than 2 mm.

In another embodiment, the integrated otic microprobe according to the invention comprises a cap that fits within a middle ear round window. The integrated otic microprobe measures substantially cochlear blood flow via the fiber optic laser Doppler flowmetry probe. The integrated otic microprobe also measures substantially compound action potentials of cranial nerve VIII via the electrocochleography electrode. The term "measures substantially" is defined to mean accurately detecting data signals in near real-time.

In yet another embodiment, the invention comprises a system for intraoperatively monitoring auditory function. The system comprises a hand held device for insertion into an ear. This hand held device houses an integrated, multi-membered otic fiber optic laser microprobe. Also included in the system are reference and ground electrodes, a diode laser excitation source, and a computerized data monitoring unit. An electronic control unit connects a first member of the fiber optic laser microprobe to the computerized data monitoring unit. The system also comprises a sound generator. A high input impedance bioamplifier of the system connects a second member of the fiber optic laser microprobe, the reference electrode and the ground electrode to the computerized data monitoring unit. This integrated otic fiber optic laser microprobe of the system comprises a first member comprising a fiber optic laser Doppler flowmetry probe which measures blood flow and velocity; a second member comprising an electrocochleography electrode which measures neural compound action potentials; a cap encompassing a tip of the fiber optic laser Doppler flowmetry probe; at least one irrigation lumen; at least one aspiration lumen; and a means for conducting an electrocochlear signal from the laser Doppler flowmetry probe tip encompassed by the cap to the computerized data monitoring unit. The bioamplifier amplifies, filters and transmits electrocochlear electrode responses to the computerized data monitoring unit. The laser Doppler flowmetry probe comprises at least one emission fiber and one or more sensing fibers. Said at least one emission fiber and two or more sensing fibers are housed within a needle probe. The reference electrode detects auditory brainstem responses.

In the system of the invention, the hand held device and cap preferably comprise a medical grade polymer, preferably and elastomer. Examples of suitable elastomers include polydimethylsiloxane, urethane, silicone or other flexible silicone-based polymers.

In another embodiment, the system of the invention comprises a means for conducting an electrocochlear signal. The signaling means may be a member selected from the group consisting of a metal tube surrounding the laser Doppler flowmetry probe tip and a platinum wire in direct contact with an otic round window. Other similar types of signal conducting means, such as wires and metal surfaces may be used.

Still another embodiment of the invention is a system in which at least one irrigation lumen and at least one aspiration lumen irrigate a middle ear round window cavity through the cap encompassing the tip of the fiber optic laser Doppler flowmetry probe. In such a system, the at least one irrigation lumen and the at least one aspiration lumen may be connected to a peristaltic pump.

In yet another embodiment of the invention, the system further comprises a channel for a flexible endoscope comprising a fiber bundle for illumination, and a fiber optic imaging system including an objective lens and a flexible imaging bundle. In such a system, the flexible endoscope preferably has an overall diameter of less than 0.8 mm.

A preferred embodiment of the invention is a method of atraumatically monitoring auditory function in a patient. This method comprises inserting into a patient's ear a microprobe comprising a fiber optic laser Doppler flowmetry probe which measures blood flow and velocity; an electrocochleography electrode which measures neural compound action potentials; a cap encompassing a tip of the fiber optic laser Doppler flowmetry probe; at least one irrigation lumen; at least one aspiration lumen; and a means for conducting an electrocochlear signal from the laser Doppler flowmetry probe tip encompassed by the cap to the computerized data monitoring unit. Upon insertion into the patient's ear canal, the cap of the microprobe is positioned against the round window membrane of the middle ear. Positioning the microprobe in this manner enables measuring cochlear blood flow via the laser Doppler flowmetry probe and measuring compound action potentials of cranial nerve VIII via the electrocochleography electrode following stimulation of an auditory response with a noise at a predetermined frequency and loudness. Auditory function may then be assessed by comparing measured blood flow and compound action potential values against baseline blood flow and compound action potential values taken prior to the auditory response is stimulated.

BRIEF DESCRIPTION OF THE DRAWINGS

Various embodiment of the invention are illustrated using the same reference numerals for identical structures in the accompanying drawings in which.

DETAILED DESCRIPTION OF THE INVENTION

In order to circumvent the problem associated with the variable thickness of promontory bone among species, a technique was developed providing for laser-Doppler cochlear blood flow measurement through the middle ear round window membrane using the rabbit as an animal model. Rabbits were used because of the large amount of data available for comparison from previous experiments by the inventors on the effects of interruption of cochlear blood flow on otoacoustic emissions and cochlear potentials. Because of the position of the membrane in the human round window niche, an integrated microprobe was designed, which can be endoscopically guided through a simple myringotomy into the niche, and positioned for measurements of cochlear blood flow and cochlear potentials, with the future capability of laser treatment and suction.

An embodiment of the monitoring system comprises an optic and electric sensing probe with the associated opto-electronic processing system and a fiberoptic endoscope system for probe placement. The sensing part of the otic probe comprises two main elements:

(i) a fiber-optic laser-Doppler flowmetry probe to measure blood flow and velocity. The fiber-optic probe will be integrated into a hand held probe made that will be placed in contact with the round window to monitor ear function during neurosurgery; and (ii) a thin EcochG electrode to measure auditory compound action potentials. Fiber-optic endoscope system for probe placement will be developed together with the related electronics for the dedicated monitoring device.

An otic microprobe integrating an EcochG electrode with a laser-Doppler velocimetry probe has been designed and built to be anatomically compatible with the human inner ear. The laser Doppler velocimetry probe is essentially a tube housing two optical fibers with connections to electro-optical instrumentation to emit and receive laser light and calculate velocity via the Doppler principle. Laser Doppler velocimetry probes are generally known, such as the LaserFLo, produced by Vasamedics, Inc.

Figure 1:
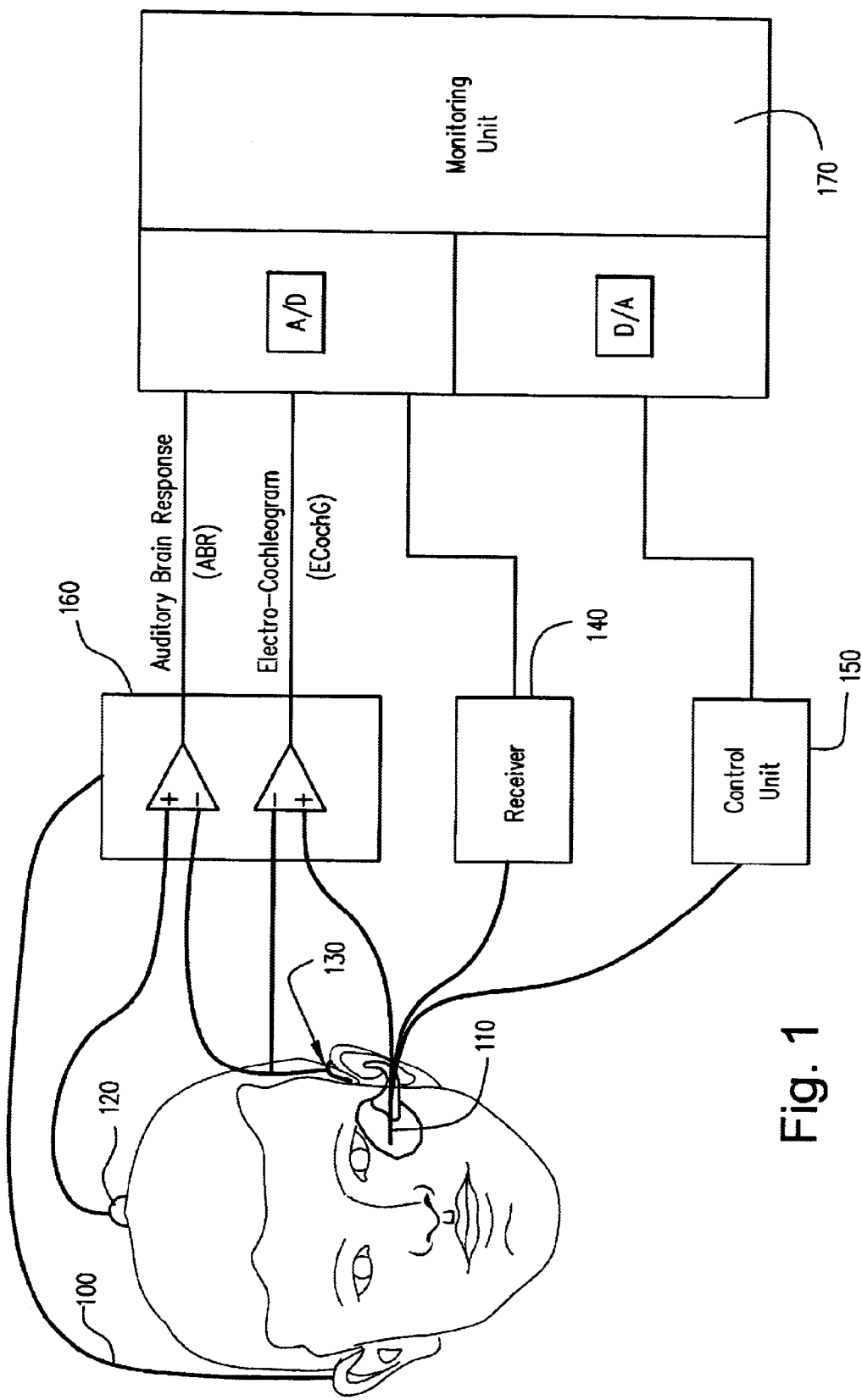
FIG. 1 is a schematic diagram of a system having components for intraoperatively monitoring auditory function.
Figure 2:
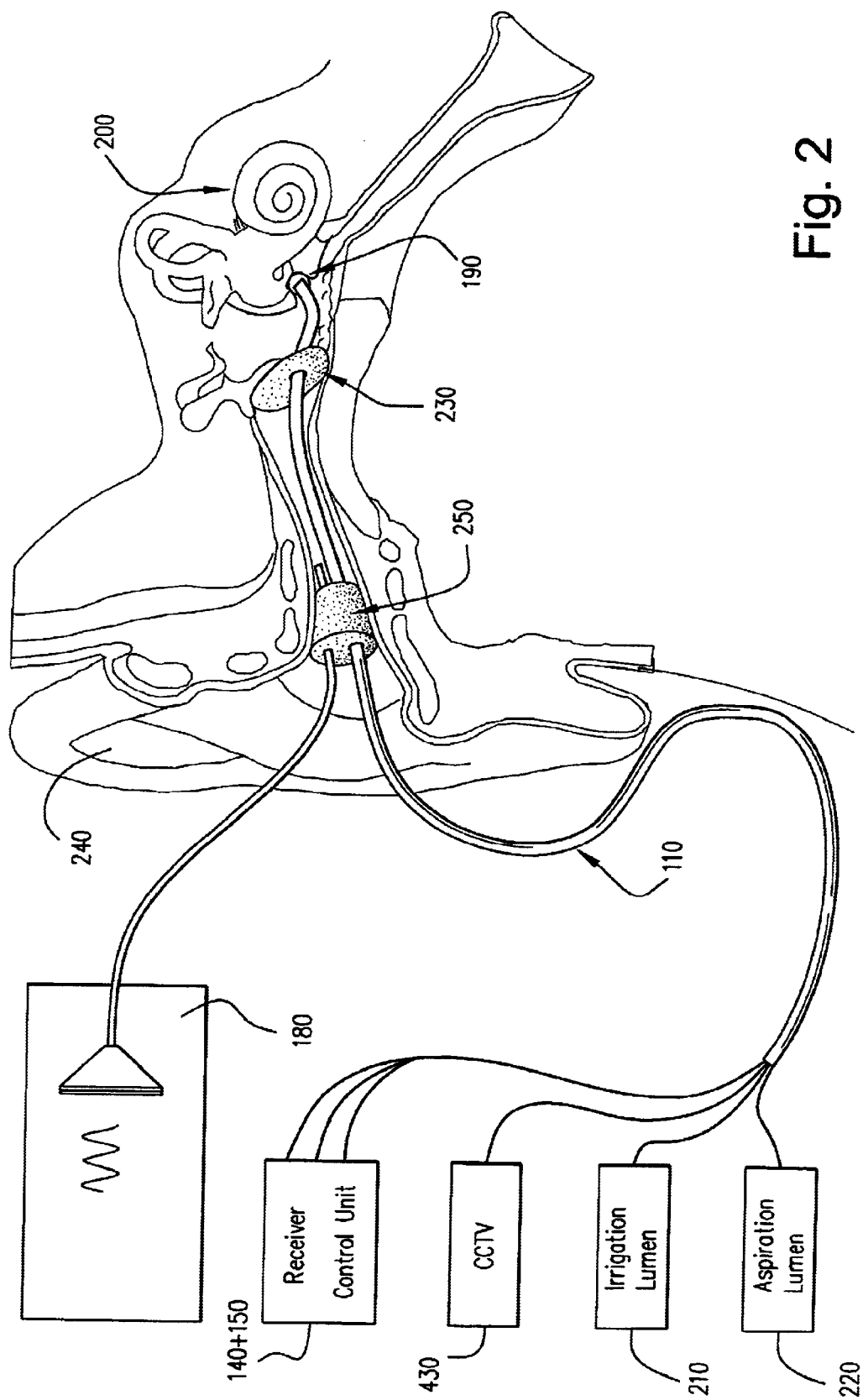
FIG. 2 depicts the placement of an otic microprobe of the invention into a patient's ear.

The principle of a clinical application of an embodiment of the integrated otic microprobe in a system for intraoperatively monitoring auditory function is shown in FIGS. 1 and 2. The system depicted in FIGS. 1 and 2 comprises an integrated, multi-membered otic fiber optic laser microprobe 110, an active auditory brain response electrode 120, and reference electrode 130, wherein the multi-membered otic fiber optic laser microprobe 110 is inserted into an ear 240 of a patient through ear drum 230 and contacting the middle ear round window 190. Components of the system may be held in place within the ear via any suitable means, such as a silicone rubber stopper 250.

As shown in FIG. 1, a laser excitation source, such as a diode laser excitation source, and receiver 140 is connected to the fiber optic laser microprobe 110 for excitation purposes. A computerized data monitoring unit 170 controls outgoing stimuli to the fiber optic laser microprobe 110 via the laser excitation source and receiver 140 and an electronic control unit 150 directing the fiber optic laser Doppler flowmetry probe within the fiber optic laser microprobe The laser excitation source and receiver 140 and an electronic control unit 150 are depicted together in a single square in FIG. 2. Auditory brain response signals detected via the active electrode 120, neural compound action potentials detected by the electrocochleography electrode within the fiber optic laser microprobe 110, and reference electrode 130 data are received by a high input impedance bioamplifier 160. A sound generator 180 is used to stimulate auditory responses for monitoring purposes. The otic microprobe is integrated into a hand-held device and will be placed in contact with the round window 190 of the middle ear to monitor ear function during the experimental surgical procedures. The round window 190 may be irrigated during such procedures to improve cochlear blood flow measurements using at least one irrigation lumen 210 and at least one aspiration lumen 220 contained within the fiber optic laser microprobe 110.

Reference electrode 130 and ground electrode 100 are connected to the input of differential bioamplifier 160, which amplifies and filters differential electrocochleography signals. The light signals collected by collection fibers of the laser Doppler probe are transformed using an electro-optical system, into electrical signals that undergo preliminary processing in the fiber optic laser microprobe 110. Preprocessed EcochG and laser-Doppler signals are sent to the computerized data monitoring unit 170, where these signals are digitized, further processed, and displayed on a computer or video monitor for intraoperative monitoring. The computerized data monitoring unit 170 will also synchronize the sound generator output and the collection signals generated in response to the acoustic excitation.

Figure 3:
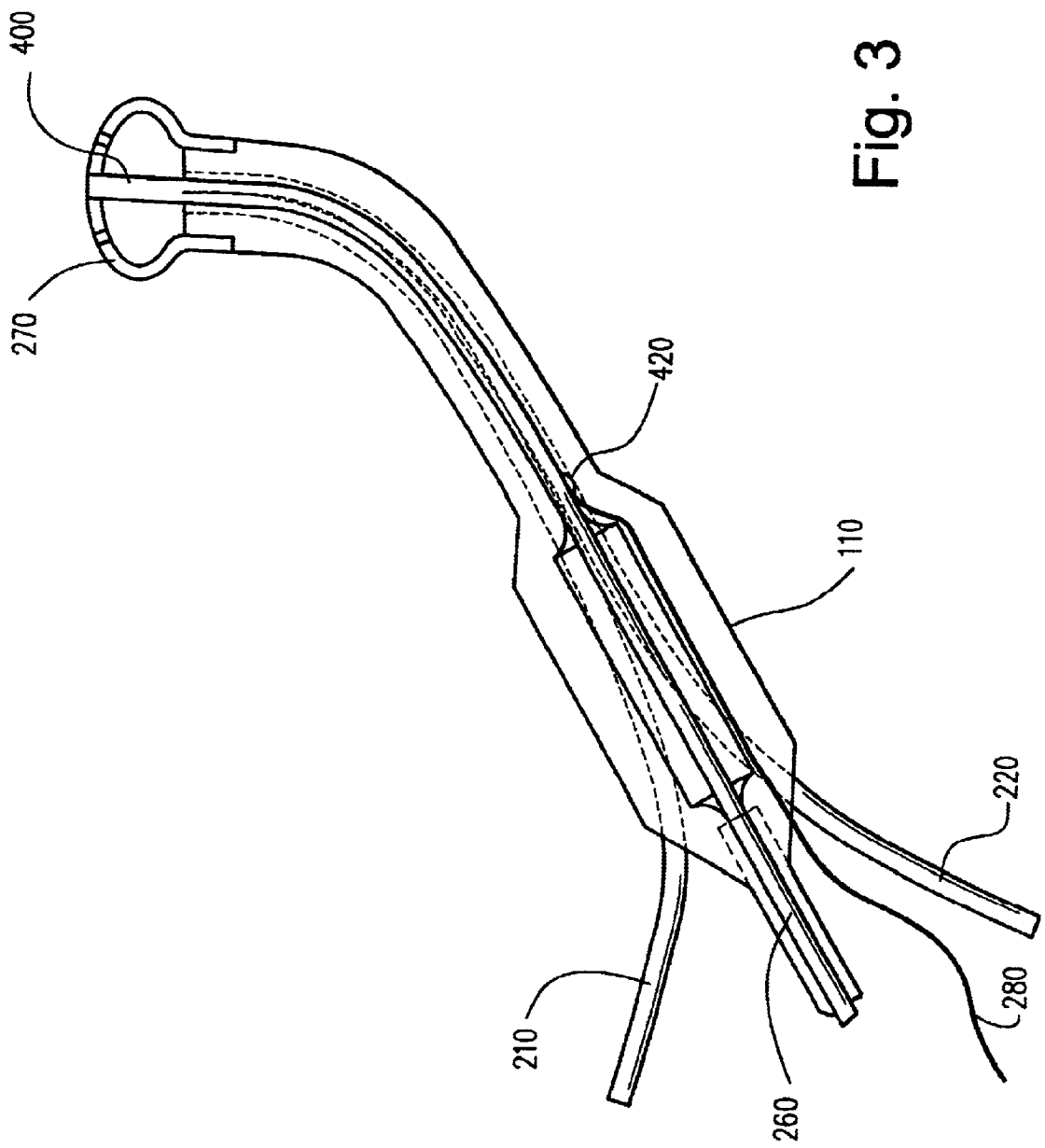
FIG. 3 depicts an embodiment of the otic microprobe of the invention in which the means for conducting an electrocochlear signal comprises a platinum wire.

An embodiment of the integrated fiber optic laser microprobe 110 is shown in FIG. 3. In this embodiment, a laser-Doppler velocimetry probe 260 is integrated into the fiber optic laser microprobe 110, together with at least one irrigation lumen 210 and at least one aspiration lumen 220. The irrigation lumen 210 and the aspiration lumen 220 may have an inner diameter of about 0.3 mm. The irrigation lumen 210 is for irrigating the round window cavity through an elastomeric cap 270 housing the tip of the laser-Doppler velocimetry probe 260, while the aspiration lumen 220 serves to remove excess fluid. Lumens 210 and 220 may be connected to larger bore silastic tubes (1.65 mm inner diameter) to minimize flow resistance and allow for connection to a peristaltic pump. The laser-Doppler velocimetry probe 260 integrates at least one emission fiber and two sensing fibers into a miniature needle probe. The fiber optic laser microprobe 110 is activated by a an excitation source, such as a solid-state laser, a 780 nm diode laser, a gas laser at 633 nm, or other suitable near-infrared or visible laser sources. Currently in use is a similar probe for blood flow measurements in animals.

A laser-Doppler velocimetry probe 260 with a 0.8 mm diameter, 30 mm long tip will be used in this embodiment. Both the hand-piece containing the laser-Doppler velocimetry probe 260 and the elastomeric cap 270 housing the tip of the laser-Doppler velocimetry probe 260 will be made of a medical grade polymer, such as silicone rubber. The polymeric components may be manufactured by injection molding using custom designed molds.

An ECohG signal may be detected via a means for conducting an electrocochlear signal from the laser Doppler flowmetry probe tip encompassed by elastomeric cap 270 to the computerized data monitoring unit. Transfer of electrocochlear signals may be accomplished by, for example, a stainless steel tube 400 surrounding the laser-Doppler tip that is in contact with the membrane of the round window and connected to the amplifier 160 via an insulated wire 280. Preferably, an EcochG signal is picked up via stainless steel tube 400, which directly contacts a middle ear round window, and conducted by Pt wire 280 soldered to stainless steel tube 400 at point 420, as shown in FIG. 3. Insulated wires 280 are preferably embedded in silicone rubber or Teflon. The entire integrated fiber optic laser microprobe 110 will be electrically insulated.

Figure 4B:
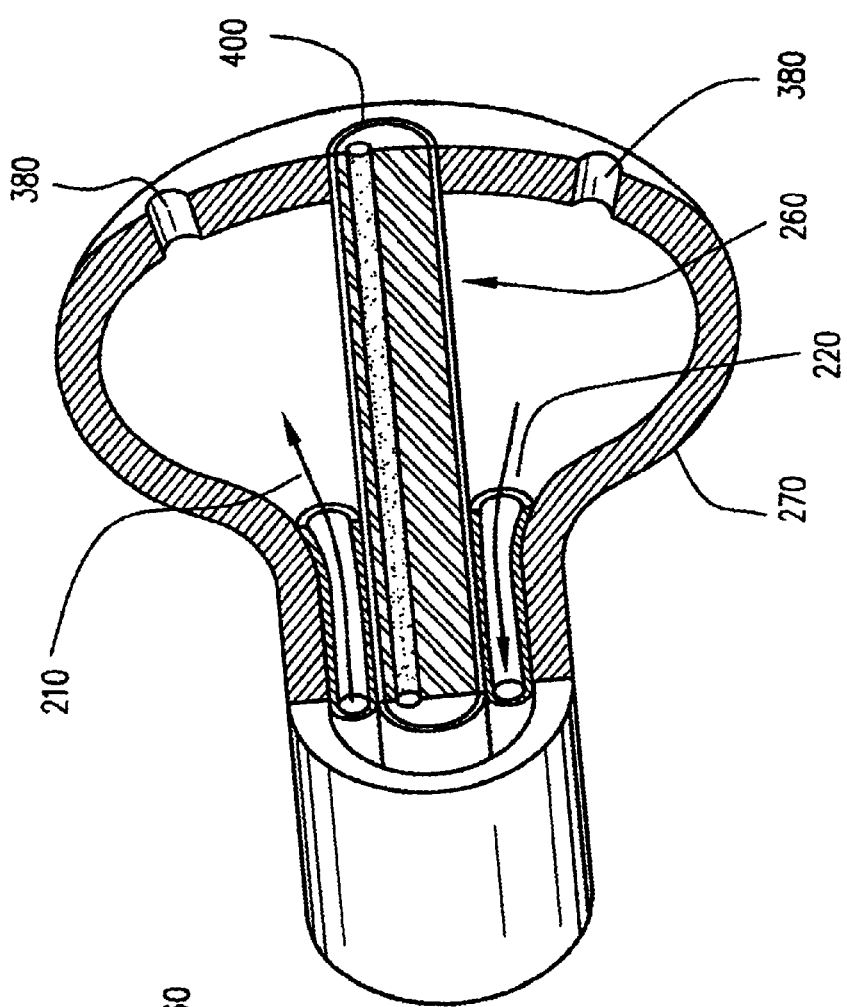
FIG. 4b is an en-face view of a microprobe's laser Doppler flowmetry probe tip encompassed by a silastic PDMS elastomeric cap.
Figure 4A:
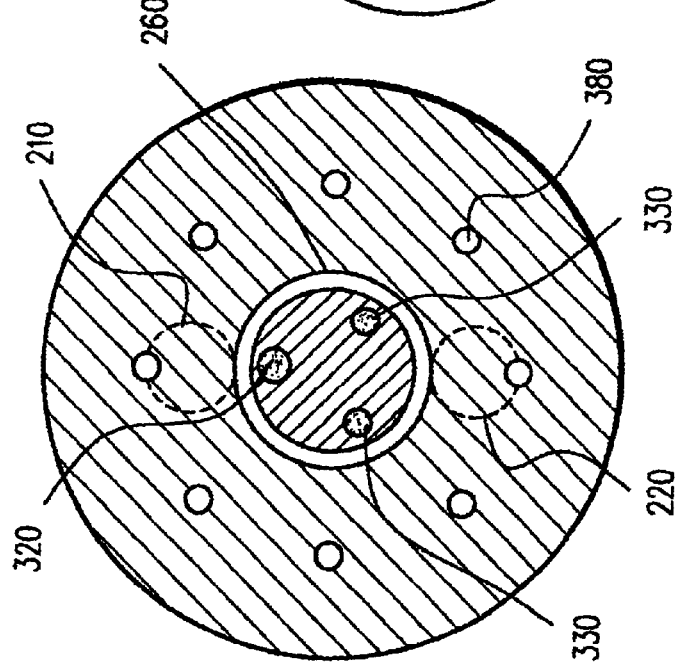
FIG. 4a is a cross sectional view of a microprobe's laser Doppler flowmetry probe tip encompassed by a silastic polydimethylsiloxane elastomeric cap.

A cross-sectional view of an embodiment of elastomeric cap 270 housing the tip of the laser-Doppler velocimetry probe 260 is shown in FIG. 4. In this embodiment, a stainless steel tube 400 is used to detect the EcochG signals. Aspiration/irrigation holes 380 located in the elastomeric cap 270 provide access to irrigation lumen 210 and aspiration lumen 220. Sensing fibers 330 and excitation fibers 320 are also shown.

In the system for intraoperatively monitoring auditory function, the laser-Doppler probe will be connected to its electronic control unit and its serial output will be connected to the Smart-EP monitoring system. EcochG electrode response will be amplified and transmitted to the Smart-EP system. This miniaturized amplifier can tolerate high electrode impedances that may result from probe placements and easily compensate impedance imbalances between inputs of the amplifier.

Initially, the Smart-EP system software will be modified to allow simultaneous acquisition of EcochG, auditory brainstem response and the laser-Doppler flow monitor data. Currently, Smart-EP, a commercial evoked potential system manufactured by Intelligent Hearing Systems, has capabilities for simultaneous EcochG and auditory brainstem response data acquisition. Modifications will be made to the current Windows-based software to monitor the serial RS232 output from the laser-Doppler flow monitor. Screens will be designed to display EcochG and auditory brainstem response recordings, and flow information as a function of time in order to monitor deleterious effects of surgical manipulation of the auditory nerve and blood supply. Algorithms will also be incorporated to automatically detect EcochG and auditory brainstem response recordings, and flow information as a function of time in order to monitor deleterious effects of surgical manipulation of the auditory nerve and blood supply. Algorithms will also be incorporated to automatically detect EcochG and auditory brainstem response peaks in order to provide easy to interpret peak latency plots that can be monitored for latency fluctuations.

In another embodiment, the integrated fiber optic laser microprobe 110 may be optimized for clinical application in humans that will also include an additional channel for endoscopy to allow accurate placement of the probe and avoid damaging the round window. The endoscope 290, shown in FIG. 5, will consist of a fiber bundle for illumination 300 and a fiber-optic imaging system 310 including an objective lens and a flexible imaging bundle. Such flexible endoscopes can be designed with an overall diameter preferably of less than about 0.8 mm. Images from the endoscopic fiber may be monitored on a video display, such as a closed circuit television (CCTV) 430 as shown in FIG. 2.

Figure 5:
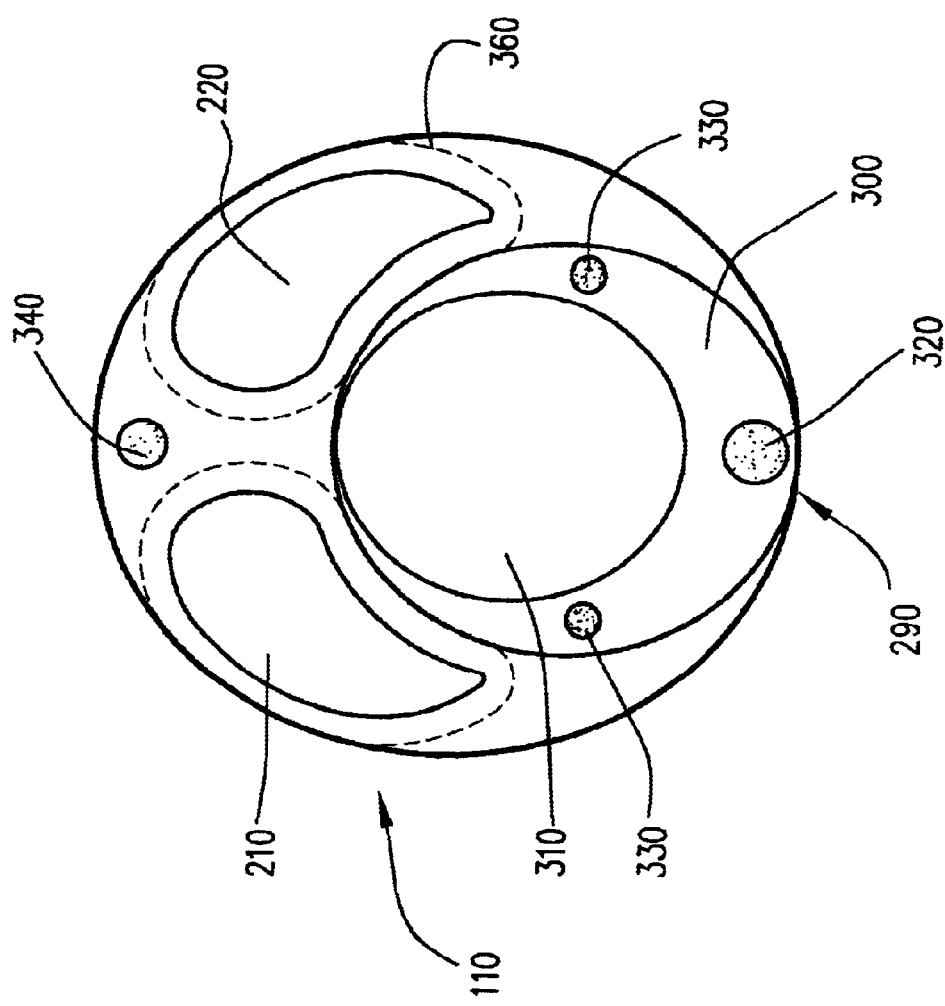
FIG. 5 depicts a cross section of an otic microprobe containing a flexible endoscope.

This embodiment of integrated fiber optic laser microprobe 110 may include irrigation and aspiration lumens 210 and 220, respectively, surrounded by an inert polymer such as silicone rubber 360, an EcochG electrode 340, as well as an excitation fiber 320 and one or two sensing fibers 330 for the laser-Doppler probe. The endoscope 290 and the laser-Doppler fibers 320 and 330 may be mounted in the same channel including illumination fibers 300, as shown in FIG. 5. The total diameter of this integrated fiber optic laser microprobe 110 will preferably be less than about 2 mm. A similar microoptical endoscopic system for microsurgical applications including illumination fibers, optical imaging channel, and an additional channel for laser energy delivery, all combined in a tip of 0.89 mm diameter (Rol et al. 1995) is known in the art. In addition, a second laser source can be coupled to excitation fiber 320 for laser treatment of tissue when necessary, for example photocoagulation of bleeding vessels. Also contemplated is photovaporization, photosensitization therapy, particularly of chemotherapeutics, and photodilation. Such an endoscopic system comprising a second laser source will also contain a means for switching between laser sources, such as an optical switch capable of switching the system from a first laser source to a second laser source for treatment of tissues.

The invention will be further illustrated by the following non-limiting examples.

EXAMPLES

Example I

Validation of the probe is to be accomplished in order to compare the flow velocimetry measurements with the laser-Doppler probe before and after integration in the otic microprobe. These measurements will demonstrate whether the slight bend and the presence of irrigation and aspiration affect the experimental results. Further comparison of the ECochG readings when the signal is detected at the stainless steel tip of the laser-Doppler probe, and when the signal is detected with a platinum wire placed directly in contact with the round window.

In a first test to validate velocimetry, measurements of fluid velocity will be performed in vitro in an experimental model of a single blood vessel. A peristaltic pump will be used to circulate water containing scattering particles (polystyrene microspheres) into a thin-walled transparent silastic tube. The inner diameter of the tube, the diameter of the microspheres, as well as the pumping pressure will be varied. Fluid flow will be measured with a standard 0.8 mm diameter, 30 mm long laser-Doppler probe and with the integrated otic microprobe of the invention. The results of the two measurements will be compared to ensure the inventive microprobe is at least as accurate as the standard laser-Doppler probe.

In a second test, the characteristics of the various embodiments of the microprobe of the invention will be investigated. A model that mimics the round window and cochlear anatomy and physiology will be designed and built using several non-conductive polymers. First, using a donor human head, a mold of the round window and surrounding tissues will be made using a vinylmethylsiloxane polymer. A 100 $\mu$m thin membrane of polyHEMA hydrogel (36% $H_2O$) will be used to mimic the elasticity and electrical conductivity of the round window membrane. To mimic the bony edges of the window, solid polymethylmethacrylate will be used. A multi-channel array of 30–150$\mu$m thin polytetrafluoroethylene-glass-polydimethylsiloxane (PDMS) tubes will be used to mimic the cochlea vasculature. To respect the human anatomical features, these elements will be assembled together in a plastic skull with non-conducting polydimethylsiloxane adhesive. The inner chamber formed by the cochlea and the inner surfaces of the round window and surrounding bony walls will be flooded with a conductive saline solution. The signal of a pulse generator will be connected to the inner chamber via a platinum wire. To mimic cochlear blood flow, the array will be connected to a three-roller peristaltic device pumping a slurry of 1–10$\mu$m diameter polystyrene microspheres that will serve as an initial model for the scattering particles (Borgos, 1990). The pump will be electronically controlled to mimic arterial and venous blood flow. The inner ear pressure will be assessed to ±1 mmHg with a piezoelectric sensor. The probe's distal end will be connected to a peristaltic pump for irrigation-aspiration, and to a laser-Doppler velocimeter (flow measurement) and its proximal tip inserted in the above-described model of the inner ear. Each probe's optical, flow, pressure and electronic parameters will be validated.

Example II

A significant amount of data from animals has been collected measuring cochlear blood flow using laser-Doppler devices. It has been observed that laser-Doppler probe location and angle within the round window niche of the rabbit can affect cochlear blood flow measurements. Also, any significant trauma to the round window membrane adversely affects the ability to obtain meaningful data. Therefore, the design of the working end of the otic microprobe will be tested within the round window niche of the rabbit.

In order to record compound action potentials, two different otic probe designs are envisioned. One design positions the EcochG on the tip of the steel tube (FIG. 4). Another design (not shown) utilizes a thin platinum wire surrounding the probe tip and embedded in the silicon rubber to measure compound action potentials.

Specifically, the ability to place the probe within the round window niche atraumatically will be assessed. In addition, the variability of cochlear blood flow and compound action potential values will be obtained for different angles of probe placement and after multiple placements into the same round window to assess consistency of measurements. The angle and size of the distal end of the otic microprobe may be modified based on the data obtained in this series of tests.

The inventive otic microprobe will be used in a series of experiments using six rabbit ears to measure cochlear blood flow and compound action potentials without any other manipulations to the animal. The rabbit preparations will be similar to those described previously (Widick, et al. 1994). Briefly, after appropriate anesthesia, the rabbit will be stabilized using a screw mounted head holder the dorsal neck muscles will be sectioned and resected at the midline to provide adequate access to the posterior basal skull region. The auditory bulla (middle ear) will be opened from the posterior to expose the round window niche. An electric dental drill fitted with a diamond burr will be used to enter the middle ear cavity just below the horizontal border, between the bulla's thick and thin posterior walls. The upper portion of the wall will be resected gently until the cochlear round window niche is widely exposed. This approach to the bulla is known to provide reliable round window laser-Doppler cochlear blood flow measurements, and is further described in Mom et al., 1999. Using a micromanipulator, the otic microprobe will be placed in to the round window niche and against the round window membrane. Cochlear blood flow and compound action potential recordings will be made simultaneously without movement of the probe. The angle and depth of insertion into the round window niche of the probe will then be altered and measurements repeated, with any changes in cochlear blood flow and compound action potential values noted.

To measure cochlear blood flow, a commercial device (Vasamedics Inc., Laserflo BPM2) interfaced to the proposed otic probe, with a wavelength of 780 nm and optical power of 2 mW at the probe tip, will be used. Cochlear blood flow data points, which will be continuously acquired at a rate of 2 points per second, will be displayed as a smoothed function by on-board Doppler circuitry that automatically determine a running average so that mean cochlear blood flow values are computed for each 10–2 interval. These smoothed values will be acquired and stored by controlling personal microcomputer system (Smart-EP), which will be further processed for plotting and statistical analysis.

Compound action potential signals will be fed into a preamplifier and then to a commercially available computer (PC)-based evoked-response system (Smart-EP System), which provides the processing, visual display, and storage of waveform data. Stimuli will be 70–90 dB SPL broadband rarefaction clicks, presented at rates between 19 and 25 clicks per second. The number of response averages will be varied between 100 and 125 to maximize the compound action potential amplitude and to obtain a new waveform every 5 seconds. Responses will be filtered conventionally between 100 and 1500 Hz. Cochlear blood flow and compound action potential data will be plotted as a function of time using the same time scale.

The primary objective of the first experiment is to ascertain whether the prototype otic microprobe can be used to obtain laser-Doppler cochlear blood flow and compound action potential values comparable to those from previous work. The physical stability of the probe will be assessed by examining the round window niche for signs of tissue trauma after removal of the device. The design of the working end of the probe will be tested for consistency of measurements by recording cochlear blood flow and compound action potential values before and after a series of re-insertions and changes in probe tip angle. Cochlear blood flow and compound action potential data will be transferred electronically to a commercially available spreadsheet (Microsoft Excel, v5.0). This software will be used to compute descriptive statistics specifying the means and standard deviations (SDs) of the cochlear blood flow/compound action potential values for the six ears. Parametric analysis using a commercial software package (Abacus Concepts, Statview v4.5) will be used to establish intraear differences among re-insertions and changes in probe angle using a paired t-test.

It is important to note that the flow units of cochlear blood flow are relative units of ml LD/min/100g tissue, with the term "LD" defined as the relative measurement volume of the system. The lack of absolute units of measurement is a limitation inherent to the principle of laser-Doppler based blood flow measure. The use of relative units is necessary, primarily because Doppler measurements are sensitive to all types of microenvironment, and not just that produced by the flow of red blood cells. Hence, any residual cochlear blood flow value that is registered after the eighth nerve is severed corresponds to the physiologic and non-physiologic background noise floor of the preparation. The two EcochG electrode designs will be compared based in the compound action potential measurements obtained from rabbit experiments and the most favorable prototype otic probe will be used for cochlear blood flow blockage experiments.

Example III

In the second experiment, the otic microprobe will be used to systematically measure changes in cochlear blood flow and compound action potential during interruption of cochlear blood flow by compressing the internal auditory artery. The experiment will mimic the clinical situation of monitoring blood flow to the inner ear and auditory function during operations to remove acoustic neuromas and other tumors around the brainstem. Results obtained with the microprobe may then be compared to those using otoacoustic emissions, ABR and blood flow measurements from previous work conducted by the inventors.

The results from eight test rabbit ears will be obtained. The animals will be prepared in the same manner as those used in Experiment I. Access to the round window will be obtained as described above. In order to compress the internal auditory artery, a suboccipital approach will b e employed to visualize the porus acousticus of the internal auditory canal, performed as described by Widick et al. (Widick et al., 1994). Once the sensor probe is in place in the round window niche, and the CPA region exposed, a custom fabricated glass micropipette will be maneuvered by hand or micromanipulator to compress the eighth cranial nerve complex, and thus effectively compromise the blood supply to the cochlea. Obstructing the entire nerve ensures that all labyrinthine branches of the AICA are occluded.

Prior to the onset of the compression period, baseline values of both cochlear blood flow and compound action potentials will be obtained over a period of one to several minutes. Cochlear blood flow and compound action potentials will be measured simultaneously, as in Experiment 1, during each occlusion episode. To allow the cochlea to recover from an ishemic event, the compressions will be released, and the post-ischemic time course of the cochlear blood flow/compound action potential responses will be tracked for about ten minutes. Data will consist of determining the delay in seconds for cochlear blood flow and compound action potential levels to change by more than two standard deviations from baseline values at the onset of the obstruction, and to return to within two standard deviations of their corresponding pre-occlusion readings during the post-occlusion recovery period. Other measures that will be derived from these data using the spreadsheet software described below include the slopes of both the onset and offset functions in order to specify the rates of change in the response measures during the critical ischemic stages.

For every test ear, after a systematic series of transient ischemic episodes has been performed, the entire eighth nerve bundles, including the labyrinthine vessels, will be completely severed at the level of the porus acousticus to ensure that, in the absence of cochlear blood flow, the LD signal decreases to the noise floor. Lastly, the animal will be euthanized using an overdose of anesthetics, and a final measure of cochlear blood flow obtained. Data will be stored as in Experiment 1.

Specific data will consist of the delay in seconds for cochlear blood flow and compound action potentials to change by more than two standard deviations from baseline values at the onset of the obstruction, and to return to within two standard deviations of their corresponding pre-occlusion readings during the post-recovery period. Analysis of variance (ANOVA) will be utilized to compare cochlear blood flow and compound action potential onset and offset times and slopes of those functions. These data will be compared with those previously obtained by the inventors to ensure that otic microprobes provide similar values of cochlear blood flow and compound action potentials during these experimental conditions.

The test animals will be ten pigmented New Zealand rabbits, approximately 5 males and 5 females, ranging in weight from 2–4.5 Kg (ages 6–8 months). The animals will be subjected to a protocol approved as being in compliance with appropriate animal use guidelines. Rabbits were selected as the test animal of choice because these animals have long been used as experimental models for hearing research, and thus a substantial amount of known data is available for comparison purposes. Rabbits are particularly suited for hearing research, as they are physiologically robust, and tolerate the effects of anesthesia over lengthy experimental sessions. This attribute is important due to the need to make repeated measurements over lengthy time courses in order to obtain intra-subject measurements for control and experimental data. Ten animals are to be used in two different experiments in order to replicate results and to obtain repeated measured for statistical analysis.

A surgical level of anesthesia in the presence of spontaneous respiration will be induced in all rabbits by an intramuscular (IM) injection of a mixture of ketamine hydrochloride (50 mg/kg) and xylazine hydrochloride (10 mg/kg). Levels of anesthesia will be monitored by recording animal heart rates. At regular 40 minute intervals, pain and blink reflexes will be tested to ensure the animals are adequately anesthetized during the entire protocol. All procedures subsequent to the initial induction of anesthesia will be performed within a walk-in sound-treated chamber. Core-body temperature will be maintained around 38° C. using a thermostatically controlled blanket with feedback provided by a rectal thermometer. The head of each test animal will be secured by a surgically implanted head mount device enabling the head to be securely oriented at any given angle. Most of the surgical procedures will be performed using an operating microscope.

At the end of each experimental protocol, test rabbits will be euthanized using an overdose of (75 mg/kg) of sodium pentobarbital injected intravenously through the lateral ear vein.

Auditory compound action potentials will be collected from rabbits using the modified Smart-EP system with the proposed otic probe. Auditory brainstem responses will be collected using the same stimulation probe and three small recording needle electrodes placed on the rabbits head. The data acquisition and stimulation procedure proposed in this study is routinely conducted for hearing evaluation. The blood supply to the cochlea will be manipulated as typically done during acoustic neuroma surgery. While under general anesthesia, the cerebellopontine angle will be exposed via a posterior craniotomy created utilizing a dental drill by a neurosurgeon. A glass beaded pipette, mounted on a micromanipulator, will be used to compress the internal auditory artery to various levels and for various durations. At the end of each experiment, the animals will be sacrificed. The research will determine which technique provides the best measure of cochlear status for intraoperative monitoring in order to reduce hearing loss known to be associated with these procedures.

Example IV

The otic probe will be placed into the ear of a patient undergoing surgery to remove a tumor around the hearing nerve (such as an acoustic neuroma). As the dissection of the tumor proceeds, blood flow and evoked potentials will be monitored for changes indicating potential damage to the inner ear or lack of circulation thereto.

During use, the probe will be placed through an incision in the eardrum of a patient with sudden hearing loss, using local anesthesia. Blood flow to the cochlea and evoked potential will be measured. Medications can be introduced either through the irrigation port of the probe or systemically, for example, intravenously. Improvements in blood flow and evoked potentials can then be recorded. Since the procedures according to the invention can be performed under local anesthesia, the inventive process can be practiced in a doctor's private office, outpatient clinic, surgicenter, day hospital, or any other outpatient facility. The procedure can also be performed in a surgical setting, such as an operating suite, during more serious or invasive surgery.

In a clinical setting, the otoprobe will be used to simultaneously assess cochlear blood flow and cochlear potentials (EcochG). It is anticipated that these measurements will be useful in the treatment of patients with a variety of cochlear disorders of hearing loss, including, but not limited to, the following: sudden sensorineural hearing loss, Meniere's disease, cochlear hydrops, noise exposure-related hearing loss, ototoxicity and tinnitus. Cochlear blood flow measurements from affected ears of individual patients may be compared to both normative average values and measures obtained from the normal contralateral ear of the same patient, using velocity of liquid flow. EcochG waveforms may be interpreted in a standard fashion to obtain action potential values and summating potential values in microvolts. Measurement of cochlear blood flow and EcochG with the otoprobe of the invention should aid in the diagnosis of hearing loss or otic disorders. The inventive otoprobe is further expected permit clinicians to follow a course of treatment directly, some of which may involve medications directly applied to the round window of a patient using the irrigation port of the otoprobe itself.

More specifically, topical anesthesia of the external ear canal and tympanic membrane can be effected using a variety of standard formulations, including phenol, ester or amide topical anesthetics, such as lidocaine, and the like. Using magnification and illumination, for example, a microscope or head light/loops, a radial myringotomy is created in the posterior superior quadrant of the tympanic membrane. Under direct visualization, the distal tip of the otoprobe is directed manually through the myringotomy. The middle ear may be endoscopically explored using the optical fiber/light source channels to show the anatomy on the video display. A treatment laser port may be employed to divide adhesions around the round window niche. Once the true round window membrane is identified, the tip of the probe is directed manually into the round window niche and into position in direct contact with or very near (within about 0.5 mm) to the membrane. Cochlear blood flow and EcochG measurements may be taken with the otoprobe stabilized manually or using the ear canal obturator fixation device previously described. Several measurements may be taken after minute adjustments of the otoprobe position to obtain average or maximum values. The probe is removed manually at the completion of the measurements and the myringotomy patched in standard fashion.

While the invention has been described in detail and with reference to specific embodiments thereof, it will be apparent to those of ordinary skill in the art that various changes and modifications can be made therein without departing from the spirit and scope of the invention.

The contents of all books, articles and published materials cited are incorporated herein by reference.

REFERENCES

Kilpatrick D, Tyberg JV, Parmley WW. Blood measurement by fiber optic laser Doppler anemometry. IEEE Trans BME 2(2):142–145, 1982.

Levine RA. Surgical monitoring applications of the brainstem auditory evoked response and electrocochleography. In Owen J, Donohoe, eds. Clinical atlas of auditory evoked potentials. Grune & Stratton, N.Y., 1988, pp. 103–116.

Levine RA, Ojemann RG, Montgomery WM, McGaffigan PM. Monitoring auditory evoked potentials during acoustic neuroma surgery. Insight into mechanism of the hearing loss. Ann Otol Rhinol laryngol 93: 115–123, 1984.

Mom T, Telischi FF, martin GK, Lonsbury-martin BL. Measuring cochlear blood flow and distortion product otoacoustic emissions during reversible cochlear ischemia in the rabbit model. Hear Res 133: 40–52, 1999.

Ren T, Avinash GB, Nuttall Al, Miller JM, Laurinkained EA, Quirk WS. Dynamic response of cochlear blood flow to occlusion of anterior inferior cerebellar artery in guinea pigs. J. Appl. Physiol 76:212–217, 1994.

Stem MD, Lappe DL, Bowen PD, Chimosky JE, Holloway GA jr, Keiser HR, Bvowman RL. Continuous measurement of tissue blood flow by laser-Doppler spectroscopy. Am j. Physiol 232: 441–448, 1977.

Telischi FF, Stagner B, Widick MP, Balkany TJ, Lonsbury-Martin BL. Distortion-product otoacoustic emissions monitoring of cochlear blood flow. Laryngoscope 108: 30 837-842, 1998.

What is claimed is:

1. An otic microprobe system comprising:
   an integrated unit having an insertion end and a connection end, the integrated unit comprising
      a fiber optic laser Doppler flowmetry probe constructed and adapted to measure blood flow and velocity; and
      an electrocochleography electrode;
   the connection end of the integrated unit being adapted to be coupled to an interface unit, the interface unit having
      a laser Doppler interface unit including a first laser excitation source and a laser light detector adapted to be coupled to the fiber optic laser Doppler flowmetry probe;
      a differential bioamplifier adapted to be coupled to the electrocochleography electrode; and
      a controller adapted to receive inputs from the laser Doppler interface unit and the differential bioamplifier and to generate coordinated electrocochleography and laser Doppler measurements.

2. The otic microprobe system of claim 1, further comprising:
   an endoscope disposed within the integrated unit;
   at least one aspiration lumen disposed within the integrated unit;
   at least one irrigation lumen disposed within the integrated unit;
   a visual interface unit in operational association with the interface unit, the visual interface unit adapted to be coupled to the endoscope at the connection end of the integrated unit; and
   a flexible cap disposed on an exterior surface of the integrated unit proximate to the insertion end.

3. The otic microprobe system of claim 2, wherein the flexible cap is constructed and adapted to fit within the middle ear round window to maintain an operational position of the integrated unit.

4. The otic microprobe system of claim 3, wherein the operational position of the integrated unit is a middle ear round window contacting position of the insertion end of the integrated unit.

5. The otic microprobe system of claim 2, wherein the at least one irrigation lumen and the at least one aspiration lumen are adapted to be connected to a peristaltic pump.

6. The otic microprobe system of claim 2, wherein the electrocochleography electrode is a conductive tube disposed concentrically around the fiber optic laser Doppler flowmetry probe.

7. The otic microprobe system of claim 2, wherein the electrocochleography electrode is a metal wire.

8. The otic microprobe system of claim 2, wherein exterior surfaces of the integrated unit and the flexible cap comprise a medical grade polymer.

9. The otic microprobe system of claim 8, wherein the medical grade polymer is an elastomer.

10. The otic microprobe system of claim 9, wherein the medical grade polymer comprises a member selected from the group consisting of polydimethylsiloxane, silicone rubber, and urethane.

11. The otic microprobe system of claim 2, wherein the fiber optic laser Doppler flowmetry probe includes at least one emission fiber and one or more sensing fibers.

12. The otic microprobe system of claim 11, wherein the at least one emission fiber and one or more sensing fibers are disposed within a needle probe.

13. The otic microprobe system of claim 2, wherein the electrode detects auditory brainstem responses.

14. The otic microprobe system of claim 2, wherein the endoscope comprises a fiber bundle for illumination and a fiber optic imaging system including an objective lens and a flexible imaging bundle.

15. The otic microprobe system of claim 2, further comprising a second laser excitation source and a switch for switching between the first and second laser excitation sources, the second laser excitation source being adapted to effect treatment of tissue.

16. The otic microprobe system of claim 15, wherein the treatment of tissue is a member selected from the group consisting of photocoagulation, photovaporization, photosensitization and photoablation.

17. The otic microprobe system of claim 2, further comprising a sound generation unit.

18. The otic microprobe system of claim 2, wherein the integrated unit has a diameter of less than about 2 mm.

19. The otic microprobe system of claim 1, further comprising at least one lumen.

20. The otic microprobe system of claim 1, further comprising at least one lumen disposed within the integrated unit.

21. A method of monitoring auditory function in a patient comprising:
inserting an integrated otic microprobe unit having an insertion end and a connection end, the integrated otic microprobe unit comprising
a fiber optic laser Doppler flowmetry probe constructed and adapted to measure blood flow and velocity; and
an electrocochleography electrode into a patient's ear;
positioning the insertion end of the integrated otic microprobe unit in an operational position;
stimulating an auditory response from the patient;
measuring cochlear blood flow using the fiber optic laser Doppler flowmetry probe;
measuring compound action potentials of cranial nerve VIII using the electrocochleography electrode; and
assessing auditory function by comparing measured cochlear blood flow and measured compound action potentials with baseline measured cochlear blood flow values and baseline measured compound action potentials.

22. An otic microprobe comprising:
an integrated unit having an insertion end and a connection end, the integrated unit comprising:
a fiber optic laser Doppler flowmetry probe constructed and adapted to measure blood flow and velocity, wherein the fiber optic laser Doppler flowmetry probe comprises at least one emission optical fiber and one or more sensing optical fibers; and
an electrocochleography electrode.

23. An otic microprobe system comprising:
an integrated unit having an insertion end and a connection end, the integrated unit comprising:
a fiber optic laser Doppler flowmetry probe constructed and adapted to measure blood flow and velocity, and
an electrocochleography electrode,
and wherein the integrated unit is connected to instrumentation to measure the blood flow and velocity.

24. The otic microprobe of claim 22, further comprising at least one irrigation lumen and at least one aspiration lumen disposed within the integrated unit.

25. The otic microprobe of claim 22, further comprising an endoscope disposed within the integrated unit.

26. The otic microprobe of claim 22, further comprising a cap disposed on an exterior surface of the integrated unit proximate to the insertion end, the cap being constructed and adapted to fit within a middle ear round window to maintain an operational position of the integrated unit.

27. The otic microprobe of claim 22, wherein the integrated unit has a diameter of less than about 2 mm.

28. The otic microprobe of claim 22, wherein the fiber optic laser Doppler flowmetry probe is constructed and adapted to measure cochlear blood flow and velocity.

29. The otic microprobe of claim 22, wherein the electrocochleography electrode is constructed and adapted to measure compound action potentials of cranial nerve VIII.

30. The otic microprobe of claim 22, further comprising at least one lumen.

31. The otic microprobe of claim 22, further comprising at least one lumen disposed within the integrated unit.

32. The otic microprobe of claim 23, further comprising at least one irrigation lumen and at least one aspiration lumen disposed within the integrated unit.

33. The otic microprobe of claim 23, further comprising an endoscope disposed within the integrated unit.

34. The otic microprobe of claim 23, further comprising a cap disposed on an exterior surface of the integrated unit proximate to the insertion end, the cap being constructed and adapted to fit within a middle ear round window to maintain an operational position of the integrated unit.

35. The otic microprobe of claim 23, wherein the integrated unit has a diameter of less than about 2 mm.

36. The otic microprobe of claim 23, wherein the fiber optic laser Doppler flowmetry probe is constructed and adapted to measure cochlear blood flow and velocity.

37. The otic microprobe of claim 23, wherein the electrocochleography electrode is constructed and adapted to measure compound action potentials of cranial nerve VIII.

38. The otic microprobe of claim 23, wherein the fiber optic laser Doppler flowmetry probe comprises at least one emission optical fiber and one or more sensing optical fibers.

39. The otic microprobe of claim 23, further comprising at least one lumen.

40. The otic microprobe of claim 23, further comprising at least one lumen disposed within the integrated unit.

* * * * *